US012721640B2

(12) United States Patent
Vale

(10) Patent No.: US 12,721,640 B2
(45) Date of Patent: Sep. 1, 2026

(54) SPLINED ACCESS AID FOR ASPIRATION CATHETERS

(71) Applicant: NEURAVI LIMITED, Galway (IE)

(72) Inventor: David Vale, Galway (IE)

(73) Assignee: NEURAVI LIMITED, Galway (IE)

( * ) Notice: Subject to any disclaimer, the term of this patent is extended or adjusted under 35 U.S.C. 154(b) by 78 days.

(21) Appl. No.: 18/644,729

(22) Filed: Apr. 24, 2024

(65) Prior Publication Data

US 2025/0331872 A1 Oct. 30, 2025

(51) Int. Cl.
*A61B 17/22* (2006.01)
*A61B 17/00* (2006.01)

(52) U.S. Cl.
CPC ........ *A61B 17/22* (2013.01); *A61B 17/00234* (2013.01); *A61B 2017/00238* (2013.01); *A61B 2017/00305* (2013.01); *A61B 2017/00318* (2013.01); *A61B 2017/00367* (2013.01); *A61B 2017/00778* (2013.01)

(58) Field of Classification Search
CPC .............. A61B 17/00234; A61B 17/22; A61B 2017/00238; A61B 2017/00305; A61B 2017/00318; A61B 2017/00367; A61B 2017/00778; A61B 17/221; A61B 2017/2212; A61B 2017/2215; A61B 2017/2217; A61B 2017/22035; A61B 2017/22041
USPC .......................................................... 606/127
See application file for complete search history.

(56) References Cited

U.S. PATENT DOCUMENTS 4,108,162 A * 8/1978 Chikashige .............. A46B 3/18 600/569
2008/0167678 A1* 7/2008 Morsi ............ A61B 17/320725 606/200
2010/0211087 A1* 8/2010 Osborne ........ A61B 17/320725 606/159
2014/0090642 A1* 4/2014 Bagwell ................ A61M 16/04 128/202.13

(Continued)

FOREIGN PATENT DOCUMENTS

WO 2004/107965 A2 12/2004

OTHER PUBLICATIONS

International Search Report and Written Opinion dated Aug. 1, 2025, in corresponding Application No. PCT/IB2025/054220, and submitted herewith.

*Primary Examiner* — Jocelin C Tanner
(74) *Attorney, Agent, or Firm* — Troutman Pepper Locke LLP

(57) ABSTRACT

A catheter comprises a proximal end, a distal end and a lumen. The catheter has a first outer diameter. The distal end of the catheter is flared radially outwardly to a second outer diameter. An elongated core is disposed within the lumen of the catheter. A plurality of fins are connected to the core. Each fin is resilient and projects radially outwardly from the outer surface of the core and terminates in a radially outwardly directed free end. The core is axially movable with respect to the catheter between a first position where the plurality of fins are completely located within the first outer diameter portion of the catheter and a second position where some of the plurality of fins are located within the second outer diameter portion of the catheter and some of the plurality of fins are located distally beyond the distal end of the catheter.

18 Claims, 8 Drawing Sheets

(56) References Cited

U.S. PATENT DOCUMENTS

2019/0038300 A1* 2/2019 Savastano ............. A61M 25/09
2020/0078029 A1 3/2020 Hansen et al.
2021/0187244 A1 6/2021 Buck et al.
2023/0380850 A1 11/2023 Vale et al.

* cited by examiner

FIG. 2
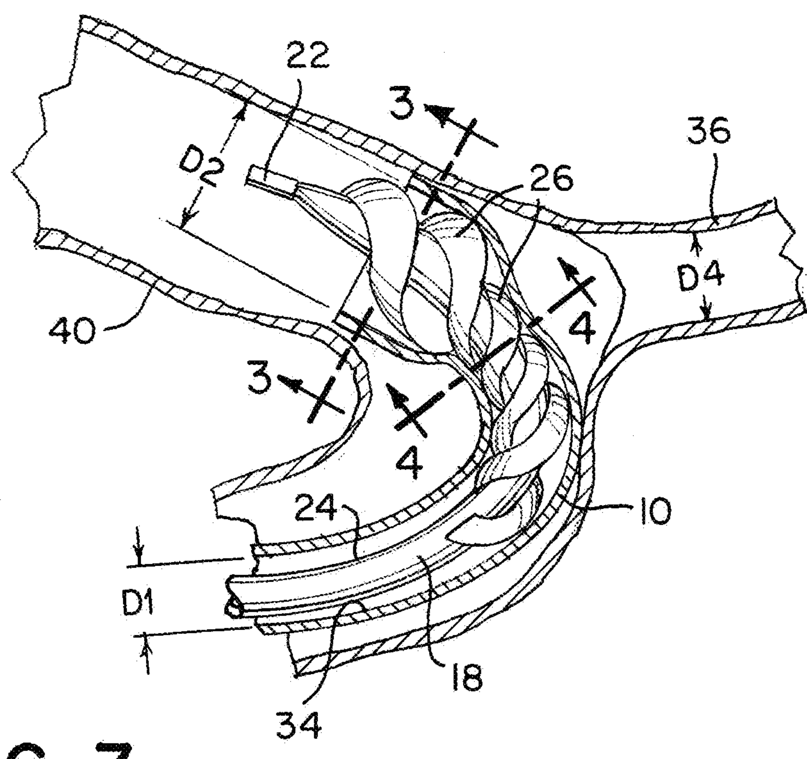
FIG. 3
FIG. 4
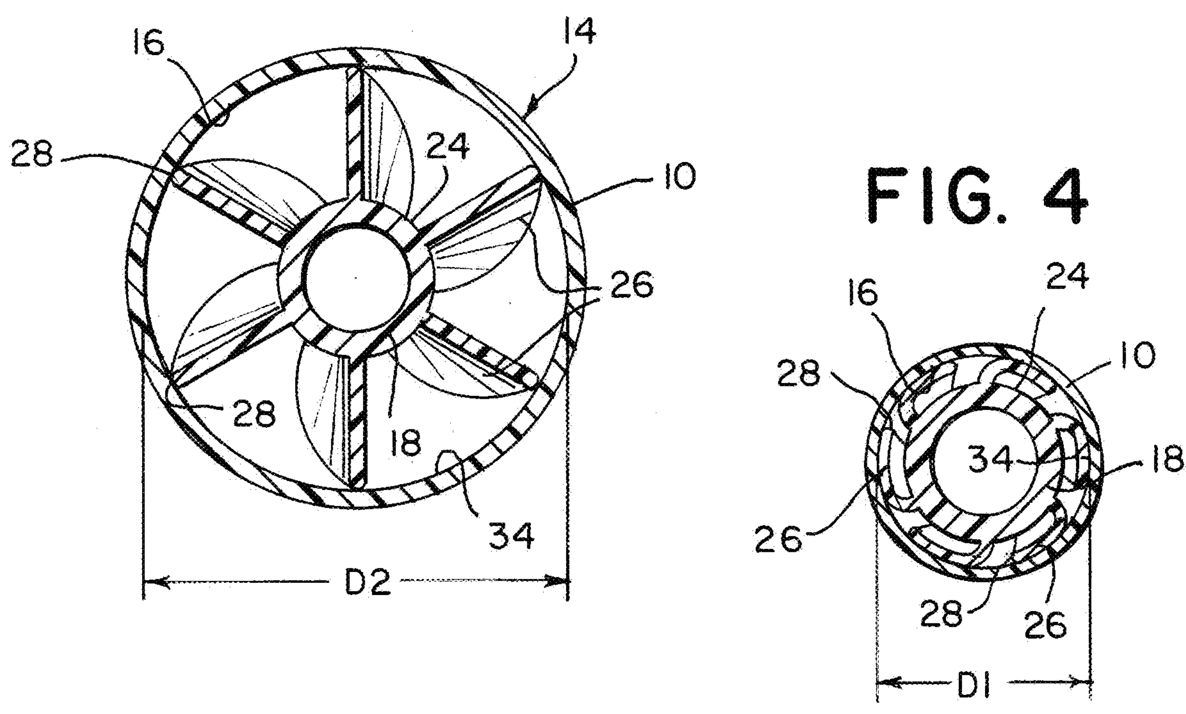

18
28
28
26
26
22

18
24
26
22
26
28
28
32
26

28
24
18
22
26
32
28

D1
24
26
28
22
10
14
D2

20
12
D1
24
10
14
D2
26
28
22

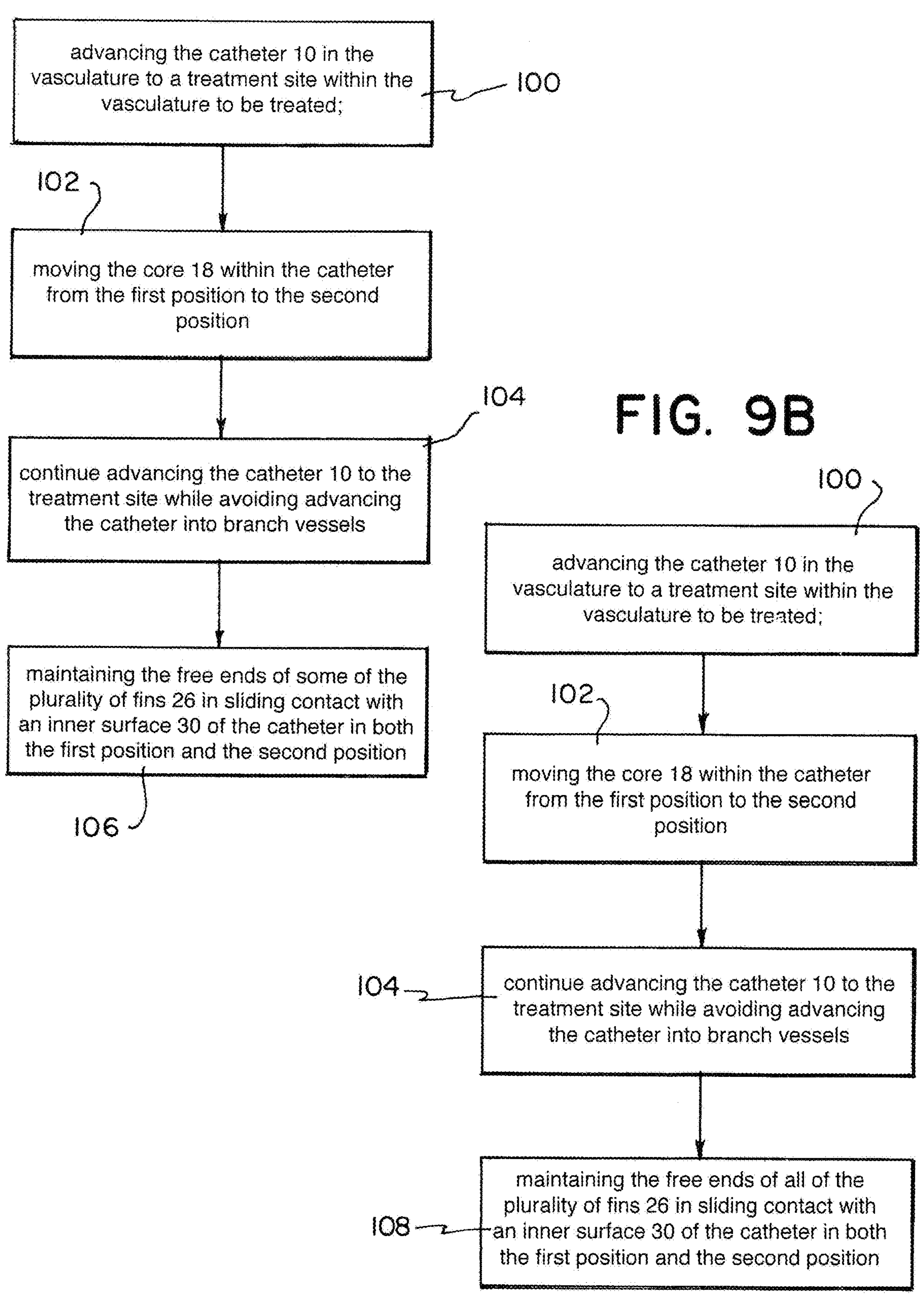
FIG. 9A
advancing the catheter 10 in the vasculature to a treatment site within the vasculature to be treated;
100
102
moving the core 18 within the catheter from the first position to the second position
104
continue advancing the catheter 10 to the treatment site while avoiding advancing the catheter into branch vessels
maintaining the free ends of some of the plurality of fins 26 in sliding contact with an inner surface 30 of the catheter in both the first position and the second position
106
FIG. 9B
100
advancing the catheter 10 in the vasculature to a treatment site within the vasculature to be treated;
102
moving the core 18 within the catheter from the first position to the second position
104
continue advancing the catheter 10 to the treatment site while avoiding advancing the catheter into branch vessels
108
maintaining the free ends of all of the plurality of fins 26 in sliding contact with an inner surface 30 of the catheter in both the first position and the second position

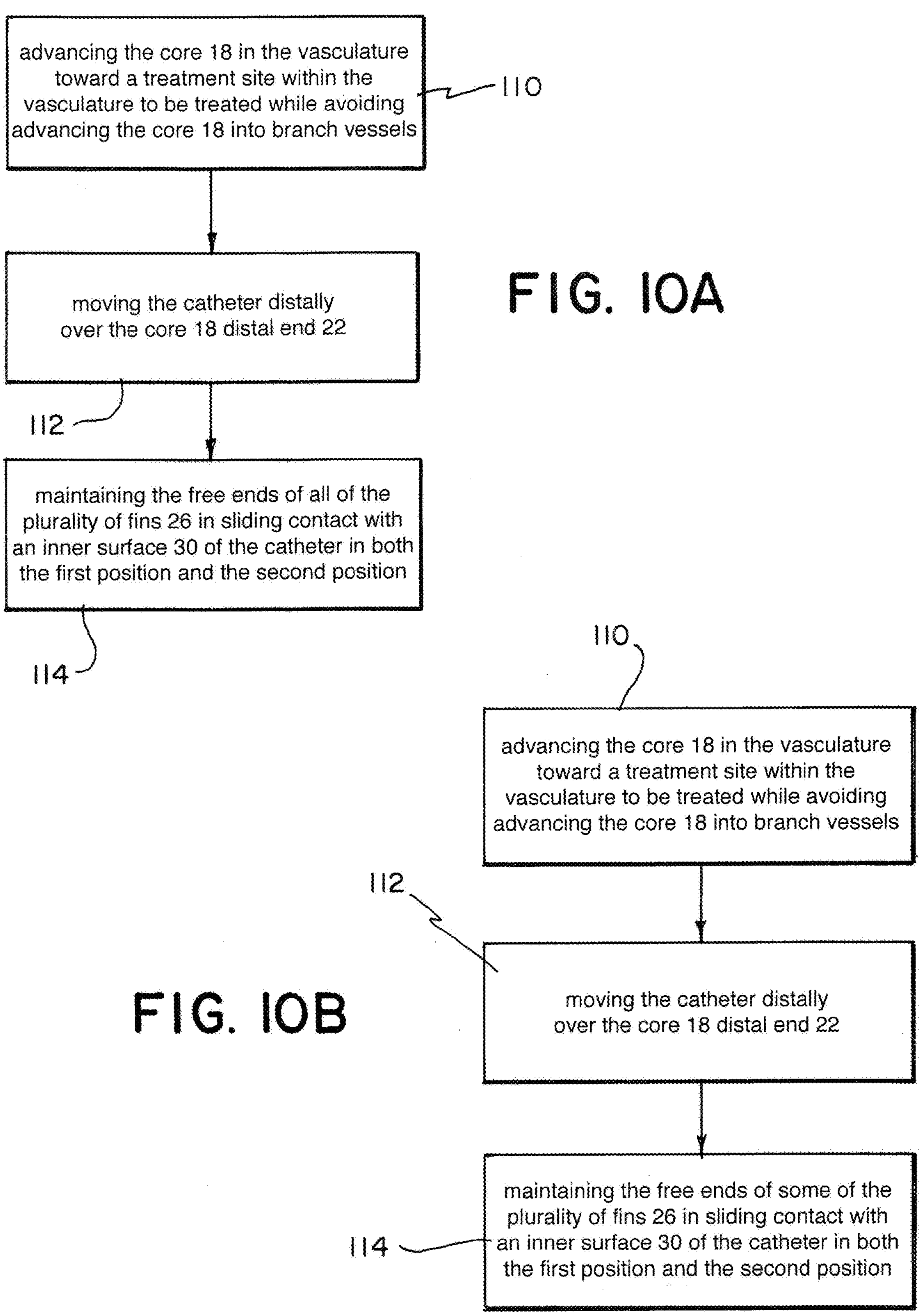
advancing the core 18 in the vasculature toward a treatment site within the vasculature to be treated while avoiding advancing the core 18 into branch vessels
110
moving the catheter distally over the core 18 distal end 22
112
maintaining the free ends of all of the plurality of fins 26 in sliding contact with an inner surface 30 of the catheter in both the first position and the second position
114
FIG. 10A
110
advancing the core 18 in the vasculature toward a treatment site within the vasculature to be treated while avoiding advancing the core 18 into branch vessels
112
moving the catheter distally over the core 18 distal end 22
maintaining the free ends of some of the plurality of fins 26 in sliding contact with an inner surface 30 of the catheter in both the first position and the second position
114
FIG. 10B

SPLINED ACCESS AID FOR ASPIRATION CATHETERS

FIELD

The present disclosure generally relates to medical instruments, and more particularly, to a catheter with enhanced navigability.

BACKGROUND

Various types of catheters have been developed for use during neurovascular interventions. No matter which specific type of catheter is selected, a catheter needs to be able to track through a specific anatomy to reach a treatment site. Then depending on the functionality of the selected catheter, an implant, another catheter, or other device may be put into and movable inside along its lumen to implement the designated task. For example, an aspiration catheter is known as an intermediate or distal access catheter. Such aspiration catheter can be used in mechanical thrombectomy procedures to perform, for example, a direct contact aspiration. In this case, an aspiration catheter navigates through the vascular anatomy to reach the occlusion site, with its proximal end connected to a syringe or aspiration pump which generates negative pressure to engage or ingest the thrombus.

During the process of navigating through the vasculature of a patient, factors such as efficiency and navigability are main factors to evaluate a performance of a catheter. Navigability is a desired character especially for distal access catheters (e.g., to ease of navigation and effective aspiration). However, this can be challenging due to the nature of the vasculature in which the catheter is navigating. Therefore, there is a need for improved or enhanced navigability for various catheters.

SUMMARY

Disclosed herein are various exemplary catheters with enhanced navigability, which may at least alleviate above needs. Also, a corresponding method for steering a catheter is provided in this disclosure.

According to an aspect of this disclosure, a catheter comprises a proximal end, a distal end and a lumen extending from the proximal end to the distal end. The catheter has a first outer diameter. The distal end of the catheter is flared radially outwardly to a second outer diameter. The second outer diameter is greater than the first outer diameter. An elongated core is disposed within the lumen of the catheter. The core has a proximal end, a distal end, and an outer surface. A plurality of fins are connected to the core. Each fin is resilient and project radially outwardly from the outer surface of the core and terminates in a radially outwardly directed free end. At least one of the free ends of the plurality of fins is in sliding contact with an inner surface of the catheter. The core is axially movable with respect to the catheter between a first position where the plurality of fins are completely located within the first outer diameter portion of the catheter and a second position where some of the plurality of fins are located within the second outer diameter portion of the catheter and some of the plurality of fins are located distally beyond the distal end of the catheter.

BRIEF DESCRIPTION OF THE DRAWINGS

The above and further aspects of this disclosure are further discussed with reference to the following description in conjunction with the accompanying drawings, in which like numerals indicate like structural elements and features in various figures. The drawings are not necessarily to scale, emphasis instead being placed upon illustrating principles of the disclosure. The figures depict one or more implementations of the inventive devices, by way of example only, not by way of limitation.

FIG. 2 is an enlarged cross-sectional view of the distal end of the catheter shown in FIG. 1.

FIG. 3 is a cross-sectional view taken along lines 3-3 of FIG. 2 and looking in the direction of the arrows.

FIG. 4 is a cross-sectional view taken along lines 4-4 of FIG. 2 and looking in the direction of the arrows.

FIG. 9A is a flow diagram illustrating exemplary method for steering a catheter according to aspects of the present disclosure.

FIG. 9B is a flow diagram illustrating another exemplary method for steering a catheter according to aspects of the present disclosure.

FIG. 10A is a flow diagram illustrating another exemplary method for steering a catheter according to aspects of the present disclosure.

FIG. 10B is a flow diagram illustrating another exemplary method for steering a catheter according to aspects of the present disclosure.

DETAILED DESCRIPTION

As used herein, the terms "about" or "approximately" for any numerical values or ranges indicate a suitable dimensional tolerance that allows the part or collection of components to function for its intended purpose as described herein. More specifically, “about” or “approximately” may refer to the range of values ±20% of the recited value, e.g. “about 80%” may refer to the range of values from 61% to 99%.

In general, various exemplary catheters described herein have enhanced navigability. With an improved navigating performance, the catheters (e.g., an aspiration catheter) can be more suitable for navigating through challenging anatomies. For example, the catheters may be easier to navigate through a cerebral vessel. Meanwhile, the catheters described in this disclosure may also be prevented from entering the ophthalmic artery. More advantages of those catheters will be conceivable and understood through detailed explanations below in conjunction with the drawings.

As used herein, the term “microcatheter” is a catheter having a diameter that is small in comparison to catheters used in cardiovascular applications, i.e., 8 French or less.

As used herein, the terms “tubular” and “tube” are to be construed broadly and are not limited to a structure that is a right cylinder or strictly circumferential in cross-section or of a uniform cross-section throughout its length. For example, a tubular structure or system is generally illustrated as a substantially right cylindrical structure. However, the tubular system may have a tapered or curved outer surface without departing from the scope of the present disclosure.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

Figure 1:
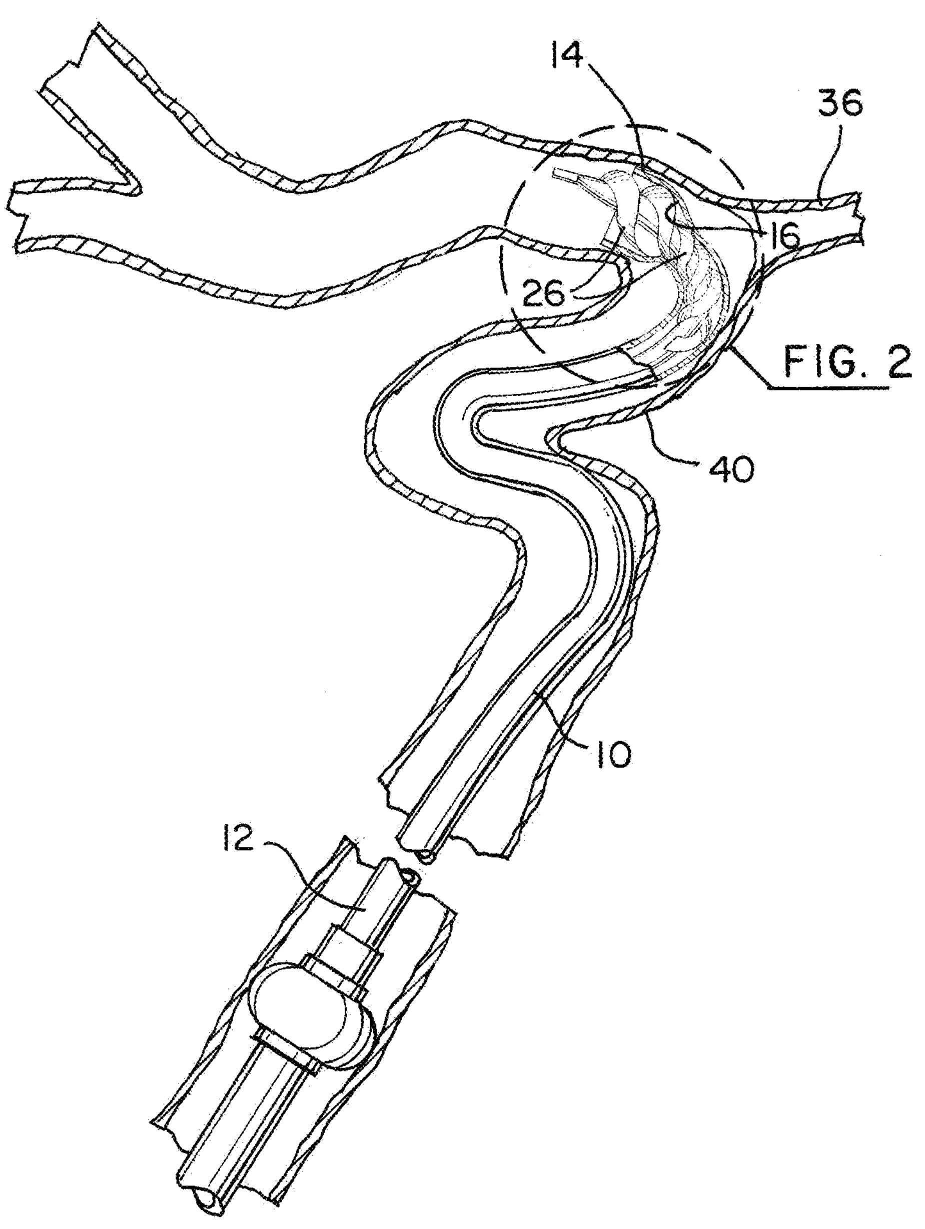
FIG. 1 is a partial cross-sectional view of a vessel having a catheter, with parts broken away at the distal end of the catheter, illustrating the catheter navigating through a vessel.

Referring now to FIGS. 1 and 2, a catheter 10 is illustrated within a cerebral vessel 40. Catheter 10 has a proximal end 12, a distal end 14 and a lumen 16 extending from the proximal end to the distal end. Catheter 10 has a first outer diameter D1 along most of its length. At the distal end 14, catheter 10 flares radially outwardly to a second outer diameter D2. Second outer diameter D2 is greater than first outer diameter D1. D1 is preferably about 0.075" to about 0.090". D1 can be, for example, about 0.084" and have an inner diameter of about 0.070". D2 is preferably about 0.095" to about 0.110". D2 can be, for example, about 0.102" and have an inner diameter of about 0.095". The flared distal end of catheter 10, which has second outer diameter D2, has an axial length of about 3 mm to about 100 mm long. In another example, the axial length of the flared distal end can be at least about 10 mm long.

Referring now to FIGS. 2-7B, catheter 10 has an elongated core 18 disposed within the lumen 16 of the catheter. Core 18 has a proximal end 20, a distal end 22 and an outer surface 24. A plurality of fins 26 are connected to core 18. Each fin 26 is resilient and projects radially outwardly from the outer surface 24 of core 18. Each fin 26 terminates in a radially outwardly directed free end 28. At least one of the free ends 28 of the plurality of fins 26 is in sliding contact with an inner surface 34 of catheter 10. In another example, all the free ends 28 of the plurality of fins 26 are in sliding contact with the inner surface 34 of catheter 10. As described above, each fin 26 is resilient such that fins are flexible and can spring back into shape in the funnel mouth portion at the distal end 14 of catheter 10. Thus, each fin 26 is in sliding contact with the inner surface 34 of catheter 10 when compressed in the smaller ID portion of the catheter D1. In addition, each fin 26 is in sliding contact with the inner surface 34 of catheter 10 when located within the flared radially outwardly distal end portion of catheter 10 that has the second outer diameter D2. As shown in FIG. 2, the second outer diameter D2 of catheter 10 is greater than an average inner diameter D4 of an ophthalmic artery 36 to prevent the catheter 10 from entering the ophthalmic artery 36. Fins 26 can be relatively soft and thick, or harder and thinner, and still have similar stiffness. In an example, fins 26 can have a Shore A hardness of between about 40A and 25D but could be as stiff as 55D. The second outer diameter D2 of catheter 10, in combination with core 18 being in a second position as described below, can also prevent catheter 10 from entering other branch vessels as the catheter is tracking toward a location within the vessel to be treated.

Figures 7A, 7B:
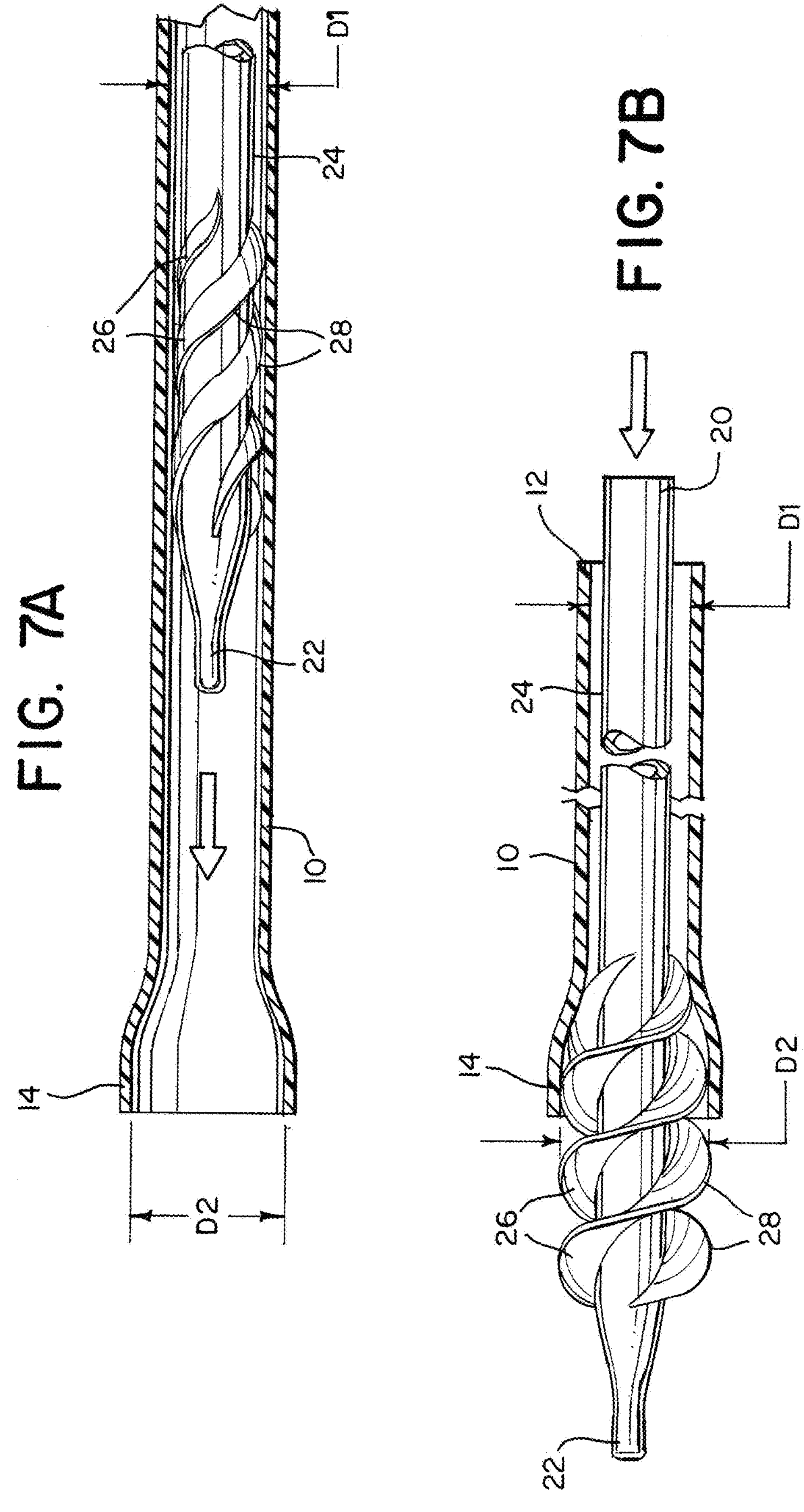
FIG. 7A is a cross-sectional view of the distal end of the catheter showing the plurality of fins completely located within the first outer diameter portion of the catheter.
FIG. 7B is a cross-sectional view of the distal end of the catheter showing a portion of the plurality of fins located within the second outer diameter portion of the catheter and another portion of the fins extending distally from the distal end of catheter.

Core 18 is axially movable with respect to catheter 10 between a first position, shown in FIG. 7A, where the plurality of fins are completely located within the first outer diameter D1 portion of the catheter and a second position where the plurality of fins 26 are located such that a portion of the fins 26 are located within the second outer diameter D2 portion of the catheter and another portion of the fins 26 extend distally from the distal end of catheter 10, as shown in FIG. 7B.

Core 18 has a central lumen 32 extending from the proximal end 20 of core 18 to the distal end 22 of core 18. Core 18 can be made from, for example, nylon, polyurethane, PEBAX® or other materials. Preferably a PTFE liner is fixedly connected to the inner cylindrical surface, so that, for example, a guidewire can move well within core 18. The fins 26 are prefably made from an elastomer such as NEUSoft™ or Chronoprene® for good shape recovery but could made from the same material as core 18 for ease of manufacturing. Core 18 has a Shore A Hardness ranging from 40A about to about 72D. In the example shown in FIGS. 1-4, each of the plurality of fins 26 has a spiral shape about the outer surface of core 18. As shown in FIGS. 1-4, at least some of the free ends 28 of each of the plurality of fins 26 are in sliding contact with an inner surface 30 of the catheter in both the first position and the second position. As shown in FIGS. 1-4 and 7A and 7B, in another example, all the free ends 28 of each of the plurality of fins 26 are in sliding contact with an inner surface 30 of the catheter in both the first position and the second position.

Figures 5, 6A, 6B:
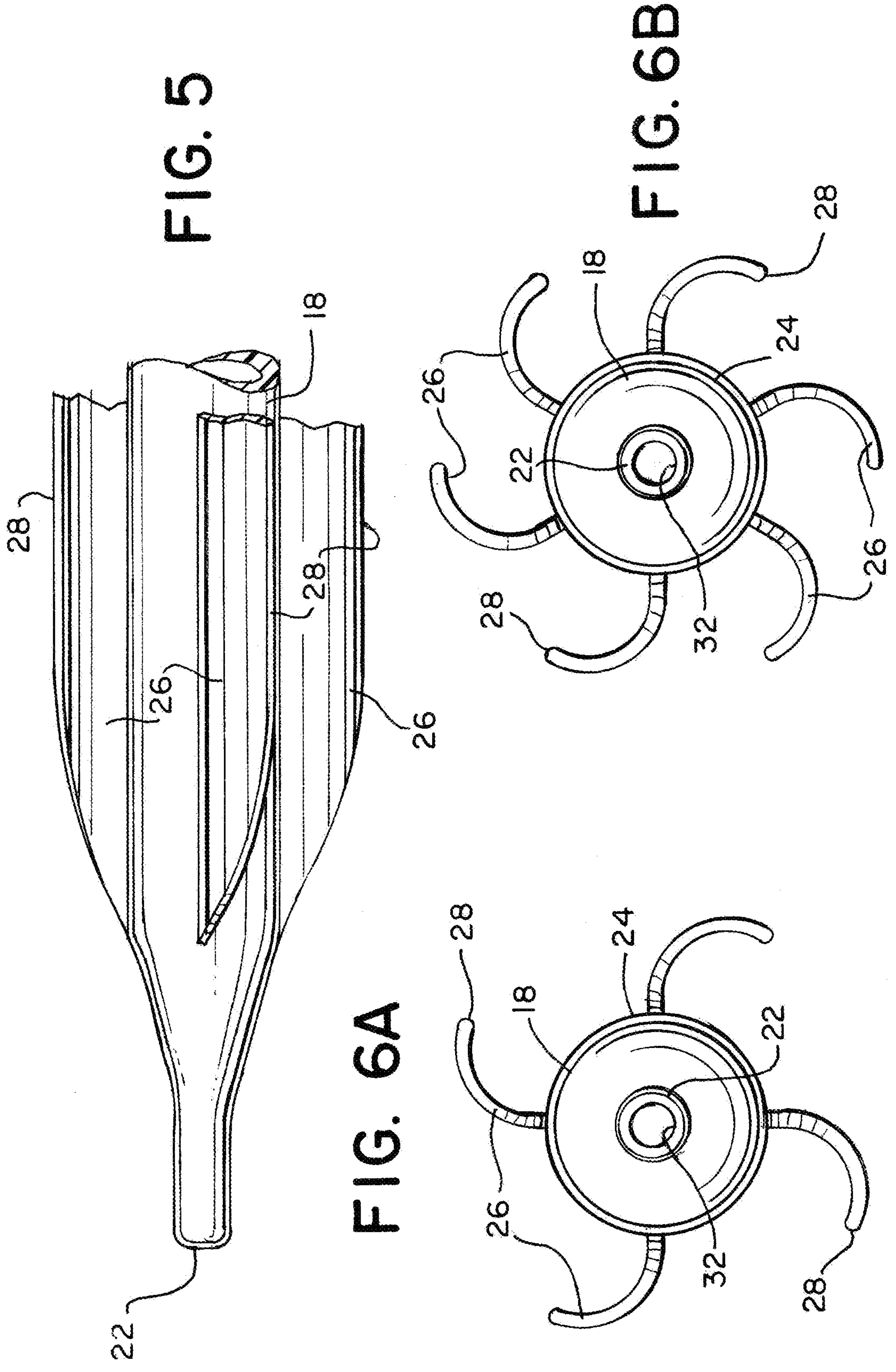
FIG. 5 is a plan view of the distal end of the catheter.
FIG. 6A is a cross-sectional view of the distal end of the catheter shown in FIG. 5.
FIG. 6B is a cross-sectional view of the distal end of an alternative embodiment of the catheter shown in FIG. 5.

Referring now to FIGS. 5, 6A and 6B, in some examples, there are four fins 26 connected to core 18 as shown in FIG. 6A. As shown in FIG. 6B, in some examples, there are six fins 26 connected to core 18. In each example, the fins 26 are spaced apart equally about the circumference of outer surface 24. In the example shown in FIGS. 5, 6A and 6B, each of the plurality of fins 26 project radially outwardly from core 18 and have an axial shape about the outer surface 24 of core 18. In other words, fins 26 are linearly disposed on the outer surface 24 of core 18 and extend in the axial direction. These fins 26 do not have a spiral shape as the fins in the example of FIGS. 1-4 do. As shown in FIG. 6A, in an example, there are four fins 26 connected to core 18 that are in sliding contact with an inner surface 34 of catheter 10 in both the first position and the second position. As shown in FIG. 6B, in another example, there are six fins connected to the core 18 that are in sliding contact with an inner surface 34 of catheter 10 in both the first position and the second position.

In an example, core 18 is in the second position which allows the distal end 14 of catheter 10 to steer around bends in the vasculature. Therefore, core 18 may cause the distal end 14 and therefore the catheter 10 to navigate easier around bends, avoiding entering a wrong vasculature path, such as, for example, the ophthalmic artery, where it's not desired to enter. FIGS. 1 and 2 illustrate a scenario where the catheter 10 navigates through a vascular system. As illustrated in FIGS. 1 and 2, the vascular system comprises a cerebral vessel 40, wherein an ophthalmic artery 36 branches from the cerebral vessel 40 at a bifurcation. Because core 18 is within the distal end 14 of catheter 10, it is easier for catheter 10 to steer around the bifurcation and bypass by the ophthalmic artery 36. Moreover, the distal end 14 of the catheter 10, having the larger diameter D2 is maintained in the open position as shown in FIG. 2 because the core 18 and its resilient fins 26 apply a radially directed outward force on the internal surface 34 of catheter 10. The open distal end 14 of catheter 10 may further assist the distal end 14 when being navigated around bends, branches, or the like (e.g., the branch formed around a bifurcation). To navigate through the cerebral vessel 40, the outer diameter D2 of the distal end 14 of catheter 10 is larger than D4, the inner diameter of an average ophthalmic artery. As discussed above, D2 is preferably about 0.095" to about 0.110". For example, the mean inner diameter of the ophthalmic artery for men is 1.43±0.24 mm, and 1.34±0.20 mm for women. As an example, the mean average inner diameter D4 of an ophthalmic artery can be 1.38±0.23 mm at an entrance to an optical vessel, which is measured at about 5 mm from origin. Note that since 1.43 mm is equal to about 0.056" and 1.34 mm is equal to about 0.053". Thus, the diameter D2 of the distal end of catheter 10 is larger than the inner diameter of an ophthalmic artery. Considering there is no statistically significant difference in diameter for gender or age, a same outer diameter D2 may be used for various patients. But it is to be understood that such parameter may be designed differently as needed, to accommodate for different medical needs of different ages and genders if there are variations in the size of the ophthalmic artery so long as D2 is larger than the diameter of the ophthalmic artery.

Figure 8A:
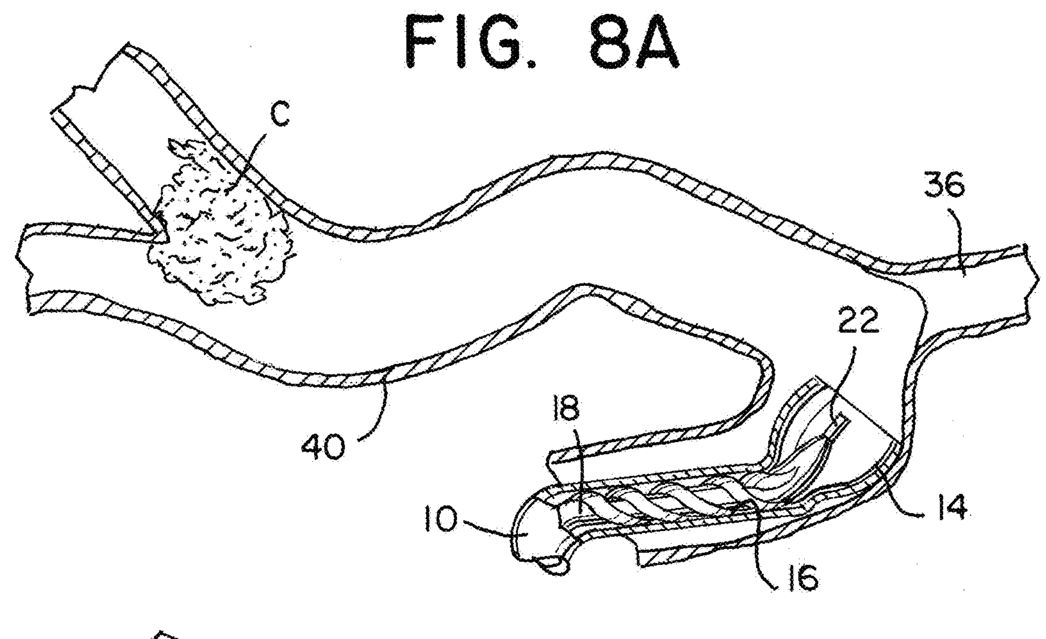
FIG. 8A is a cross-sectional view of the distal end of the catheter within a vessel and showing the plurality of fins completely located within the catheter and the catheter distal end located spaced from a branch vessel.
Figure 8B:
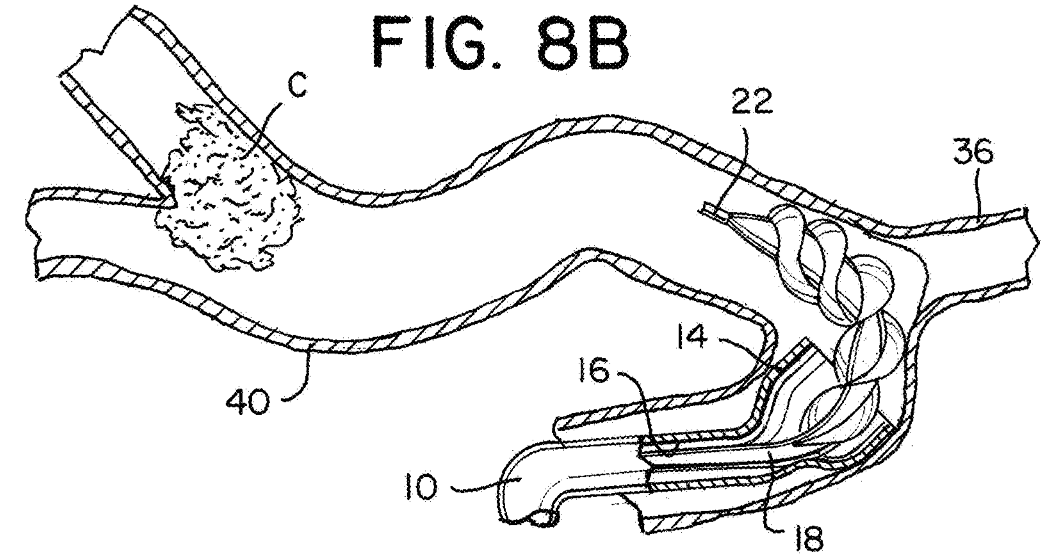
FIG. 8B is a cross-sectional view of the distal end of the catheter within a vessel and showing a portion of the plurality of fins located distally from the distal end of the catheter and distal of the branch vessel.
Figure 8C:
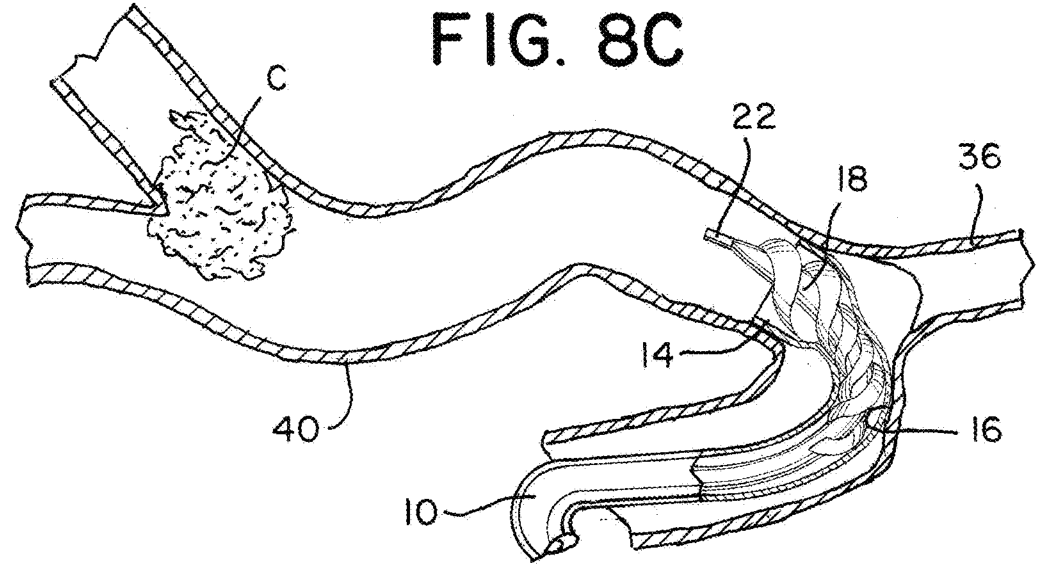
FIG. 8C is a cross-sectional view of the distal end of the catheter within a vessel distal of the branch vessel and showing a portion of the plurality of fins located within the second outer diameter portion of the catheter.
Figure 8D:
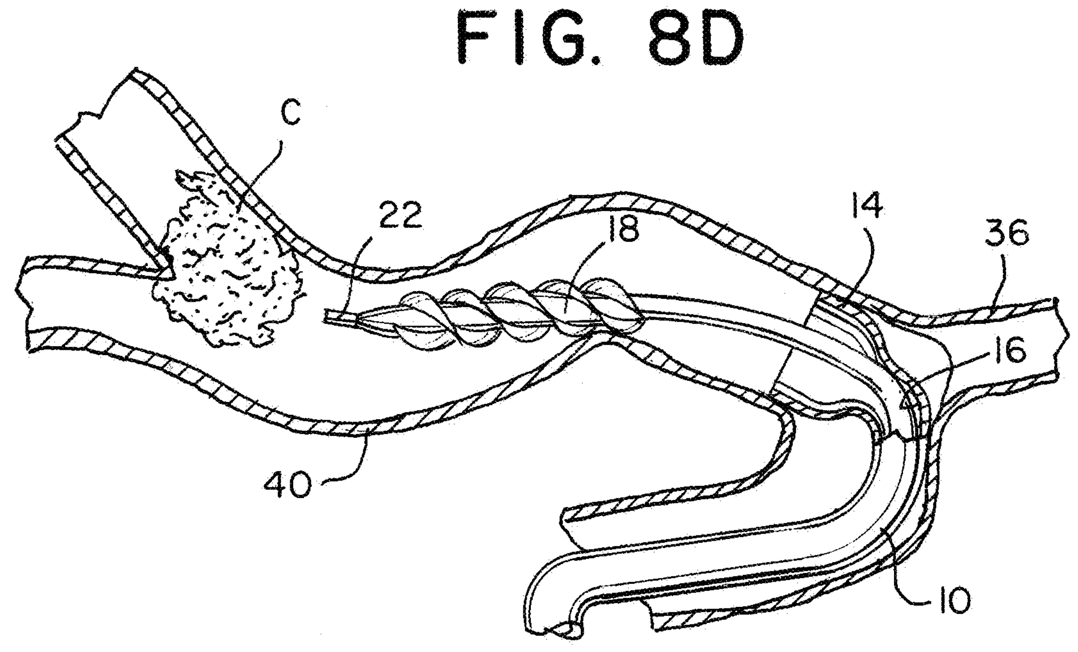
FIG. 8D is a cross-sectional view of the distal end of the catheter within a vessel and showing the plurality of fins located distally from the distal end of the catheter and proximal of a clot.
Figure 8E:
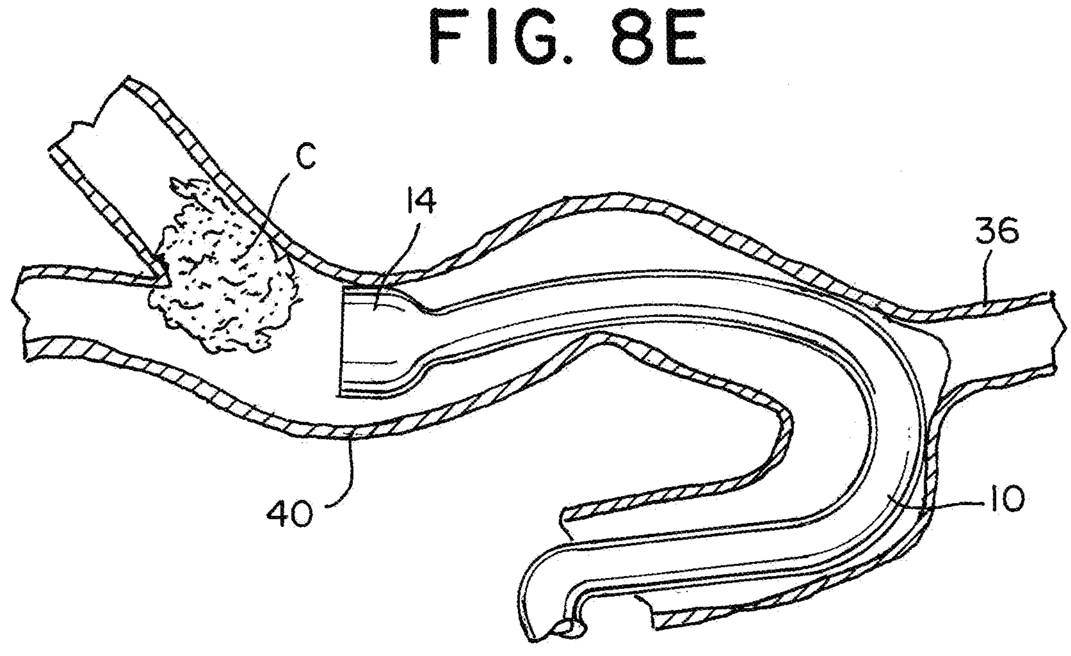
FIG. 8E is a cross-sectional view of the distal end of the catheter within a vessel distal of the branch vessel, proximal of a clot and showing the plurality of fins located within the catheter.

Referring now to FIGS. 8A, 8B, 8C, 8D, and 8E, catheter 10 is shown as it is being advanced within vessel 40 to a position just proximal of a clot C. As shown in FIG. 8A, the distal end 14 of catheter 10 is located within vessel 40 proximal of a branch vessel 36, which can be, for example, the ophthalmic artery. In the position shown in FIG. 1, the plurality of fins 26 are completely located within catheter 10 and the catheter distal end 14 is located spaced from a branch vessel 36. To prevent the catheter from entering branch vessels while being advanced within the vessel 40 on the way to the treatment site, core 18 can be advanced from the position shown in FIG. 8A to the position shown in FIG. 8B where the distal end 22 of core 18 is within vessel 40 distal from the branch vessel 36. Thus, a portion of the plurality of fins 26 are located distally from the distal end of the catheter and are distal of the branch vessel 36. Once the core has passed the branch vessel 36, catheter 10 can be advanced over the core 18 from the position shown in FIG. 8B to the position shown in FIG. 8C to a position where the distal end 14 of catheter 10 is within vessel 40 distal from the branch vessel 36. In the position illustrated in FIG. 8C, a portion of the plurality of fins 26 are located within the second outer diameter portion D2 of catheter 10. Catheter 10 and core 18 can be advanced to a position proximate of a clot C lodged within vessel 40 as shown in FIGS. 8D and 8E. As shown in FIG. 8D, core 18 can be first advanced to the position proximate of clot C such that the plurality of fins 26 are located distally from the distal end 14 of catheter 10 and proximal of clot C. Catheter 10 can then be advanced to the position proximate of clot C such that the distal end 14 of the catheter 10 is disposed over core 18 resulting in the plurality of fins located within the catheter. In some alternative examples, one skilled in the art may include using a guidewire and/or a microcatheter (not shown) to aid in tracking catheter 10 and core 18 to the treatment site. The guidewire and/or the microcatheter would have a smaller outer diameter than D1 of catheter 10.

The fins 26 can fill the enlarged diameter D2 of catheter 10 to help prevent a "ledge effect" which could be a problem if trying to advance catheter 10 alone or over a much smaller guidewire or microcatheter. Fins 26 aid to fill the gap of the open distal end 14 of catheter 10 to help prevent the open distal end 14 from catching on a branch vessel, such as, for example, the ophthalmic artery. In another example of the current disclosure, catheter 10 and core 18 can be advanced together past branch vessels, such as vessel 36, to the treatment site.

In another example, the outer diameter of the fins 26 in free space can be a fraction smaller than the inner diameter of the D2 outer diameter portion of catheter 10. In one example, the D2 distal end portion of catheter 10 has an outer diameter D2 of about 0.102" and has an inner diameter of about 0.095". In this example, the outer diameter of the fins 26 can be 0.090" or about 95% of the inner diameter of the enlarged outer diameter portion D2 of catheter 10. In another example, the outer diameter of the fins 26 can be 0.086" or about 90% of the inner diameter of the enlarged outer diameter portion D2 of catheter 10. In one example, the inner diameter of the D1 portion of the catheter can be about 0.070". Thus, the fins 26 will be in contact with the inner surface of the catheter in the D1 portion of the catheter and there can be a relatively small gap between the outer diameter of the fins 26 and the inner diameter of the D2 outer diameter portion of catheter 10 with some of the fins in contact with the inner surface of the catheter in the D2 portion of the catheter and some spaced from the inner surface of the catheter in the D2 portion.

Referring now to FIGS. 9A, 9B, 10A and 10B, methods for steering a catheter 10 is illustrated. As shown in FIGS. 9A and 9B, in one aspect of the disclosure, the method comprises step 100, advancing the catheter 10 in the vasculature toward a treatment site within the vasculature to be treated. At step 102, moving the core 18 within the catheter from the first position to the second position. At step 104, continue advancing the catheter 10 to the treatment site while avoiding advancing the catheter into branch vessels. In some examples illustrated in FIG. 8A, the method can further include step 106, maintaining the free ends of some of the plurality of fins 26 in sliding contact with an inner surface 30 of the catheter in both the first position and the second position. In some other examples illustrated in FIG. 9B, the method can further include step 108, maintaining the free ends of all of the plurality of fins 26 in sliding contact with an inner surface 30 of the catheter in both the first position and the second position.

Referring now to FIG. 10A, another example of a method for steering a catheter 10 is illustrated. The method comprises step 110, advancing core 18 in the vasculature toward a treatment site within the vasculature to be treated while avoiding advancing the core 18 into branch vessels such that the core spans across a branch vessel, such as, for example, an ophthalmic artery. At step 112, moving the catheter distally over the distal end 22 of core 18. At step 114, maintaining the free ends of some of the plurality of fins 26 in sliding contact with an inner surface 30 of the catheter in both the first position and the second position.

Referring now to FIG. 10B, another example of a method for steering a catheter 10 is illustrated. The method comprises step 120, advancing core 18 in the vasculature toward a treatment site within the vasculature to be treated while avoiding advancing the core 18 into branch vessels such that the core spans across a branch vessel, such as, for example, an ophthalmic artery. At step 122, moving the catheter distally over the distal end 22 of core 18. At step 124, maintaining the free ends of all of the plurality of fins 26 in sliding contact with an inner surface 30 of the catheter in both the first position and the second position.

Aspects of the disclosure are also provided by the following numbered clauses:

Clause 1. A catheter (10) for use in vascular vessels comprising:

- the catheter having a proximal end (12), a distal end (14) and a lumen (16) extending from the proximal end to the distal end, the catheter having a first outer diameter (D1), the distal end (14) of the catheter being flared radially outwardly to a second outer diameter (D2), second outer diameter (D2) being greater than the first outer diameter (D1);
- an elongated core (18) disposed within the lumen (16) of the catheter, the core having a proximal end (20), a distal end (22) and an outer surface (24), a plurality of fins (26) connected to the core, each fin being resilient and projecting radially outwardly from the outer surface (24) of the core and terminating in a radially outwardly directed free end (28), at least one of the free ends of the plurality of fins being in sliding contact with an inner surface (34) of the catheter, the core (18) being axially movable with respect to the catheter (10) between a first position where the plurality of fins are completely located within the first outer diameter (D1) portion of the catheter and a second position where some of the plurality of fins are located within the second outer diameter (D2) portion of the catheter and some of the plurality of fins are located distally beyond the distal end (14) of the catheter (10).

Clause 2. The catheter (10) of clause 1, wherein each of the plurality of fins (26) has a spiral shape about the outer surface of the core (18).

Clause 3. The catheter (10) of any of clauses 1-2, wherein at least some of the free ends (28) of each of the plurality of fins (26) are in sliding contact with an inner surface (30) of the catheter in both the first position and the second position.

Clause 4. The catheter (10) of any of clauses 1-3, wherein all of the free ends (28) of each of the plurality of fins (26) are in sliding contact with an inner surface of the catheter in both the first position and the second position.

Clause 5. The catheter (10) of any of clauses 1-4, wherein there are four fins connected to the core (18).

Clause 6. The catheter (10) of any of clauses 1-4, wherein there are six fins connected to the core (18).

Clause 7. The catheter (10) of any of clauses 1-6, wherein the core (18) has a central lumen (32) extending from the proximal end (20) to the distal end (22).

Clause 8. The catheter (10) of any of clauses 1-7, wherein the core (18) is made of a polymer.

Clause 9. The catheter (10) of any of clauses 1-8, wherein the core (18) has a Shore A Hardness ranging from about 40A to about 25D.

Clause 10. The catheter (10) of any of clauses 1-9, wherein each of the plurality of fins each have a linear axial shape about the outer surface of the core.

Clause 11. The catheter (10) of any of clauses 1-10, wherein at least some of the free ends of each of the plurality of fins are in sliding contact with an inner surface of the catheter.

Clause 12. The catheter (10) of any of clauses 1-11, wherein all of the free ends of each of the plurality of fins are in sliding contact with an inner surface of the catheter.

Clause 13. The catheter (10) of any of clauses 1-12, wherein there are four fins connected to the core (18).

Clause 14. The catheter (10) of any of clauses 1-12, wherein there are six fins connected to the core (18).

Clause 15. The catheter (10) of any of clauses 1-14 wherein the core (18) has a central lumen (32) extending from the proximal end (20) to the distal end (22).

Clause 16. The catheter (10) of any of clauses 1-15, wherein the core (18) is made of a poylmer.

Clause 17. The catheter (10) of any of clauses 1-16, wherein the core (18) has a Shore A Hardness ranging from 40A to about to about 25D.

Clause 18. The catheter (10) of any of clauses 1-17, wherein the second outer diameter (D2) is greater than an average inner diameter (D4) of an ophthalmic artery (36) to prevent the catheter (10) from entering the ophthalmic artery (36).

Clause 19. A method for steering a catheter (10), the catheter (10) comprising a proximal end (12), a distal end (14) and a lumen (16) extending from the proximal end to the distal end, the catheter having a first outer diameter (D1), the distal end (14) of the catheter being flared radially outwardly to a second outer diameter (D2), second outer diameter (D2) being greater than the first outer diameter (D1); an elongated core (18) disposed within the lumen (16) of the catheter, the core having a proximal end (20), a distal end (22) and an outer surface (24), a plurality of fins (26) connected to the core, each fin being resilient and projecting radially outwardly from an outer surface of the core and terminating in a radially outwardly directed free end (28), at least one of the free ends of the plurality of fins being in sliding contact with an inner surface of the catheter (34), the core (18) being axially movable with respect to the catheter (10) between a first position where the plurality of fins are completely located within the first outer diameter (D1) portion of the catheter and a second position where some of the plurality of fins are located within the second outer diameter (D2) portion of the catheter and some of the plurality of fins are located distally beyond the distal end (14) of the catheter (10), the method comprising the steps of:

- advancing the catheter (10) in the vasculature toward a treatment site within the vasculature to be treated;
- moving the core (18) within the catheter from the first position to the second position;
- continue advancing the catheter (10) to the treatment site while avoiding advancing the catheter into branch vessels.

Clause 20. The method for steering a catheter of clause 19, further comprising the step of:

- maintaining the free ends of some of the plurality of fins (26) in sliding contact with an inner surface (30) of the catheter in both the first position and the second position.

Clause 21. The method for steering a catheter of clause 19, further comprising the step of:

- maintaining the free ends of all of the plurality of fins (26) in sliding contact with an inner surface (30) of the catheter in both the first position and the second position.

Clause 22. A method for steering a catheter (10), the catheter (10) comprising a proximal end (12), a distal end (14) and a lumen (16) extending from the proximal end to the distal end, the catheter having a first outer diameter (D1), the distal end (14) of the catheter being flared radially outwardly to a second outer diameter (D2), second outer diameter (D2) being greater than the first outer diameter (D1); an elongated core (18) disposed within the lumen (16) of the catheter, the core having a proximal end (20), a distal end (22) and an outer surface (24), a plurality of fins (26) connected to the core, each fin being resilient and projecting radially outwardly from an outer surface of the core and terminating in a radially outwardly directed free end (28), at least one of the free ends of the plurality of fins being in sliding contact with an inner surface of the catheter (34), the core (18) being axially movable with respect to the catheter (10) between a first position where the plurality of fins are completely located within the first outer diameter (D1) portion of the catheter and a second position where some of the plurality of fins are located within the second outer diameter (D2) portion of the catheter and some of the plurality of fins are located distally beyond the distal end (14) of the catheter (10), the method comprising the steps of:
- advancing the catheter (10) in the vasculature to a treatment site within the vasculature to be treated;
- moving the core (18) within the catheter from the first position to the second position;
- continue advancing the catheter (10) to the treatment site while avoiding advancing the catheter into branch vessels.

Clause 23. The method for steering a catheter of clause 22, further comprising the step of:
- maintaining the free ends of some of the plurality of fins (26) in sliding contact with an inner surface (30) of the catheter in both the first position and the second position.

Clause 24. The method for steering a catheter of clause 22, further comprising the step of:
- maintaining the free ends of all of the plurality of fins (26) in sliding contact with an inner surface (30) of the catheter in both the first position and the second position.

Clause 25. The catheter (10) of clause 1, wherein the outer diameter of the plurality of fins (26) is about 95% of the inner diameter of the distal end (14) of the catheter (10).

Clause 26. The catheter (10) of clause 1, wherein the outer diameter of the plurality of fins (26) is about 90% of the inner diameter of the distal end (14) of the catheter (10).

The descriptions contained herein are examples of embodiments of the disclosure and are not intended in any way to limit the scope of the disclosure. As described herein, the disclosure contemplates many variations and modifications of an aspiration catheter, including using a guidewire and/or a microcatheter with the catheter and core of the current disclosure when tracking the catheter and core to the treatment site. Modifications and variations apparent to those having skilled in the pertinent art according to the teachings of this disclosure are intended to be within the scope of the claims which follow.

What is claimed is:

1. A method for steering a catheter, the catheter comprising a proximal end, a distal end and a lumen extending from the proximal end to the distal end, the catheter having a first outer diameter, the distal end of the catheter being flared radially outwardly to a second outer diameter, the second outer diameter being greater than the first outer diameter; and an elongated core disposed within the lumen of the catheter, the core having a proximal end, a distal end and an outer surface, a plurality of fins connected to the core, each fin being resilient and projecting radially outwardly from an outer surface of the core and terminating in a radially outwardly directed free end, at least one of the free ends of the plurality of fins being in sliding contact with an inner surface of the catheter, the core being axially movable with respect to the catheter between a first position where the plurality of fins are completely located within the first outer diameter portion of the catheter and a second position where some of the plurality of fins are located within the second outer diameter portion of the catheter and some of the plurality of fins are located distally beyond the distal end of the catheter, the method comprising the steps of:
- advancing the catheter in the vasculature toward a treatment site within the vasculature to be treated;
- moving the core within the catheter from the first position to the second position such that the distal end of the core is located distal of a branch vessel and the distal end of the catheter is located proximal of the branch vessel;
- advancing the catheter over the core such that the core returns to the first position and the distal end of the catheter moves past the branch vessel, thereby avoiding the branch vessel; and
- advancing the catheter to the treatment site.

2. The method of claim 1, wherein each of the plurality of fins has a spiral shape about the outer surface of the core.

3. The method of claim 2, wherein at least some of the free ends of each of the plurality of fins are in sliding contact with the inner surface of the catheter in both the first position and the second position.

4. The method of claim 3, wherein there are four or more fins connected to the core, and/or wherein the core has a central lumen extending from the proximal end to the distal end.

5. The method of claim 2, wherein all of the free ends of each of the plurality of fins are in sliding contact with the inner surface of the catheter in both the first position and the second position.

6. The method of claim 1, wherein each of the plurality of fins each have a linear axial shape about the outer surface of the core.

7. The method of claim 6, wherein at least some of the free ends of each of the plurality of fins are in sliding contact with the inner surface of the catheter.

8. The method of claim 7, wherein there are four or more fins connected to the core, and/or wherein the core has a central lumen extending from the proximal end to the distal end.

9. The method of claim 6, wherein all of the free ends of each of the plurality of fins are in sliding contact with the inner surface of the catheter.

10. The method of claim 1, wherein the second outer diameter is greater than an average inner diameter of an ophthalmic artery to prevent the catheter from entering the ophthalmic artery.

11. A method for steering a catheter, the catheter comprising a proximal end, a distal end and a lumen extending from the proximal end to the distal end, the catheter having a first outer diameter, the distal end of the catheter being flared radially outwardly to a second outer diameter, the second outer diameter being greater than the first outer diameter; an elongated core disposed within the lumen of the catheter, the core having a proximal end, a distal end and an outer surface, a plurality of fins connected to the core, each fin being resilient and projecting radially outwardly from an outer surface of the core and terminating in a radially outwardly directed free end, at least some of the free ends of the plurality of fins being in sliding contact with an inner surface of the catheter, the core being axially movable with respect to the catheter between a first position where the plurality of fins are completely located within the first outer diameter portion of the catheter and a second position where some of the plurality of fins are located within the second outer diameter portion of the catheter and some of the plurality of fins are located distally beyond the distal end of the catheter, the method comprising the steps of:

advancing the catheter in the vasculature to a treatment site within the vasculature to be treated;

moving the core within the catheter from the first position to the second position such that the distal end of the core is located distal of a branch vessel and the distal end of the catheter is located proximal of the branch vessel;

advancing the catheter over the core such that the core returns to the first position and the distal end of the catheter moves past the branch vessel, thereby avoiding the branch vessel; and advancing the catheter to the treatment site.

12. The method of claim 11, wherein each of the plurality of fins has a spiral shape about the outer surface of the core.

13. The method of claim 12, wherein all of the free ends of each of the plurality of fins are in sliding contact with the inner surface of the catheter in both the first position and the second position.

14. The method of claim 13, wherein there are four or more fins connected to the core, and/or wherein the core has a central lumen extending from the proximal end to the distal end.

15. The method of claim 11, wherein each of the plurality of fins each have a linear axial shape about the outer surface of the core.

16. The method of claim 15, wherein all of the free ends of each of the plurality of fins are in sliding contact with the inner surface of the catheter.

17. The method of claim 16, wherein there are four or more fins connected to the core, and/or wherein the core has a central lumen extending from the proximal end to the distal end.

18. The method of claim 11, wherein the second outer diameter is greater than an average inner diameter of an ophthalmic artery to prevent the catheter from entering the ophthalmic artery.

* * * * *